(12) United States Patent
Bell et al.

(10) Patent No.: US 11,559,249 B2
(45) Date of Patent: Jan. 24, 2023

(54) METHOD FOR MEASURING HAIR MOVEMENT CHARACTERISTICS

(71) Applicant: Conopco, Inc., Englewood Cliffs, NJ (US)

(72) Inventors: Fraser Ian Bell, Bebington Wirral (GB); LIyr Glyndwr Griffiths, Bebington Wirral (GB); Eric Gordon Mahers, Bebington Wirral (GB); Julie Marie Roberts, Bebington Wirral (GB); Graham John Cleaver, Bromborough Wirral (GB); Aneta Magdalena Stasik, Liverpool (GB)

(73) Assignee: Conopco, Inc., Englewood Cliffs, NJ (US)

( * ) Notice: Subject to any disclaimer, the term of this patent is extended or adjusted under 35 U.S.C. 154(b) by 458 days.

(21) Appl. No.: 16/623,166

(22) PCT Filed: Jun. 20, 2018

(86) PCT No.: PCT/EP2018/066482
§ 371 (c)(1),
(2) Date: Dec. 16, 2019

(87) PCT Pub. No.: WO2018/234412
PCT Pub. Date: Dec. 27, 2018

(65) Prior Publication Data
US 2021/0137448 A1 May 13, 2021

(30) Foreign Application Priority Data
Jun. 23, 2017 (EP) .................................... 17177722

(51) Int. Cl.
*A61B 5/00* (2006.01)
*G06Q 30/02* (2012.01)
*G06T 7/20* (2017.01)

(52) U.S. Cl.
CPC .......... *A61B 5/448* (2013.01); *G06Q 30/0201* (2013.01); *G06T 7/20* (2013.01); *A61B 5/44* (2013.01)

(58) Field of Classification Search
CPC ...... A61B 5/448; A61B 5/44; G06Q 30/0201; G06T 7/20
(Continued)

(56) References Cited

U.S. PATENT DOCUMENTS

| 2018/0184796 A1* | 7/2018 | Balooch | A46B 15/0006 |
| 2019/0150824 A1* | 5/2019 | Gerhardt | A61B 5/24 |
| 2021/0142486 A1* | 5/2021 | Bentley | G06T 7/0004 |

FOREIGN PATENT DOCUMENTS

| JP | 2014518254 | 7/2014 |
| WO | WO0168041 | 9/2001 |

(Continued)

OTHER PUBLICATIONS

Search Report and Written Opinion in PCTEP2018066482, dated Aug. 23, 2018.
(Continued)

*Primary Examiner* — Tom V Sheng
(74) *Attorney, Agent, or Firm* — Gerard J. McGowan, Jr.

(57) ABSTRACT

A method of measuring changes in hair movement characteristics, predictive of consumer response includes: i) providing an apparatus for measuring hair movement characteristics of hair; ii) measuring the hair movement characteristics using the apparatus to obtain a first hair movement characteristic; iii) applying a treatment to the hair or an assault to the hair; iv) measuring the hair movement characteristics using the apparatus after step iii) to obtain a second hair movement characteristic; v) comparing the first hair movement characteristic and the second hair movement characteristic; and vi) assessing a change in movement
(Continued)

occurring as a result of the application of the treatment or the assault.

17 Claims, 4 Drawing Sheets

(58) Field of Classification Search
USPC .......................................................... 33/512
See application file for complete search history.

(56) References Cited

FOREIGN PATENT DOCUMENTS

| WO | WO2012016352 | 2/2012 |
|----|--------------|--------|
| WO | WO2013005025 | 1/2013 |
| WO | WO2014016351 | 1/2014 |
| WO | WO2014016354 | 1/2014 |
| WO | WO2014016353 | 3/2014 |

OTHER PUBLICATIONS

Search Report and Written Opinion in EP17177722, dated Aug. 28, 2017.
Galiano, Analysing the movement of a hair swatch using vidoe and image analysis: A promising technique for exploring the dynamic properties of hair, International Journal of Cosmetic Science, 27, p. 56-62, Oct. 2014.
Velasco et al., Hair fiber characteristics and methods to evaluate hair physical and mechanical properties, Brazillian Journal of Pharmaceutical Sciences, 45:1, p. 153-162, Mar. 2009.

* cited by examiner

METHOD FOR MEASURING HAIR MOVEMENT CHARACTERISTICS

CROSS-REFERENCE TO RELATED APPLICATIONS

This application claims priority to International Patent Application No. PCT/EP2018/066482, filed on Jun. 20, 2018, and European Patent Application No. 17177722.0, filed on Jun. 23, 2017, both of which are incorporated herein by reference in their entireties.

FIELD OF THE INVENTION

The present invention relates to a method for measuring movement characteristics of hair, particularly movement of hair treated with different hair products and treatments, predictive of consumer response.

BACKGROUND OF THE INVENTION

The way in which hair moves has long been a point of interest for consumers and manufacturers of hair products, alike. Generally, a natural movement or bounce of the hair is desirable. Increasingly, hair products such as shampoo, conditioners, hair treatments and styling products are being sold along with claims that they deliver improvements to the movement and/or bounce of the hair.

However, unlike other hair parameters such as thickness or shine, determination of movement or bounce, to date, generally relies upon qualitative analysis of movement, which is based on consumer perception rather than on technical data.

With hair movement attributes becoming ever more important to consumers, and despite the prior art, there is a need to provide an improved method for assessing these hair movement characteristics that can reliably pick out differences between movement of hair treated with different hair products and treatments, so that consumers can make informed product selections.

SUMMARY OF THE INVENTION

Accordingly, in a first aspect, the invention provides a method of measuring changes in hair movement characteristics, the method comprising the steps of:

i) providing an apparatus for measuring movement characteristics of hair;

ii) measuring the movement characteristics of hair using the apparatus;

iii) applying a treatment or assault to the hair;

iv) measuring the movement characteristics of the hair resulting from step iii);

v) comparing the movement characteristics arising from step iv) with that of step ii); and vi) assessing the changes in movement occurring as a result of the application of the treatment or assault.

Preferably, steps (iii) to (vi) are repeated. Steps (iii) to (vi) may be repeated multiple times in order to assess the impact of repeated or long term exposure to the treatment or assault on the movement characteristics of hair. For example, from 2 to 20 times, preferably from 2 to 8 times.

Thus, it is possible to illustrate to a consumer the impact of everyday treatments and assaults on the movement of their hair. A consumer may thus evaluate the effectiveness of a treatment that might be applied to change the movement characteristics of their hair. The consumer is then enabled to select a product that is particularly suitable for his/her hair.

Movement of hair may comprise one or more different attributes of the hair, which are preferably selected from the group consisting of bounce, fluid movement, flexibility during movement; keeping shape/style/alignment during movement; less "weighed down" during movement, and lively movement.

Such attributes may be applicable in a number of different countries (for example, UK, US, China, Japan, Indonesia, India, Thailand and Brazil). Of course, attributes could equally be useful in all countries Some other attributes may be particularly applicable for consumers in particular countries. For example, weighty (in Thailand); Sa-Luay (in Thailand); flows beautifully/naturally (in Thailand); moves with vitality (in Indonesia), and; sarasara sensory (in Japan).

These attributes are terms that are commonly used with respect to the movement of hair, and common terms used by consumers in the description of hair movement characteristics.

The movement characteristics may be assessed by comparison to a standard or bench mark, preferably a scale. Preferably, the scale comprises indicators, for example numbers or letters, where the indicators correspond to incremental levels of movement characteristics, for example as typical for healthy hair through to damaged hair, or flyaway frizzy hair. In another preferred embodiment, the scale comprises illustrations, such as photographs or CAD images that illustrate the degree of movement in increments. Both indicators and illustrations may be used together.

The method of the invention can be used to define the hair need of an individual.

The method of the invention may be used in an educational tool, in communication with press, media or trade, at point of sale, in professional environments such as salons, and in commercial material, advertisement material and promotional material.

The Apparatus

Preferably, the apparatus comprises a rig upon which the hair is mountable, the rig operable to apply a forced oscillation to the hair; a camera for capturing images of the hair during movement of the hair sample during and after application of the forced oscillation; a computer communicably connected to the camera, the computer including a processor; such that the computer is capable of processing the captured images at the processor; and quantitative measurements of the hair can be extracted from the captured images.

The method may further comprise the step of: receiving at an input of the computer, consumer modelled data based upon consumer studies carried out using the hair switch(es). The consumer modelled data received is preferably a consumer perception value, d prime (d'), calculated by applying a Thurstonian model to the consumer perception of relative differences between two or more hair switches.

Upon receiving consumer modelled data, the processor may generate a cross-validated model which combines the quantitative measurements of the hair switches from the captured images with the consumer modelled data. Optionally, the cross-validated model is a partial least squares model which correlates the quantitative measurements from the captured images with the consumer perception values (d') extracted from the consumer modelled data.

The method may further comprise the step of applying a predictive model based upon the cross-validated model to quantitative measurements taken from new sets of hair switches, the predictive model predicting consumer responses to the new sets of hair switches based upon the cross-validated models.

The Hair

The method of the invention is carried out on a bundle of hair fibres, preferably a switch.

The hair is preferably human hair.

The Treatment or Assault

The Assault

Many assaults occur during everyday life or as part of a normal hair care regime or consumer habit.

Assaults are preferably selected from mechanical assaults, chemical assaults, environmental assaults and mixtures thereof.

Preferred mechanical assaults are combing, brushing, the application of hot irons for curling, straightening or setting and blow drying.

Preferred chemical assaults are treatments that contain chemicals that modify the hair, for example colouring treatments, bleaching, straightening treatments, relaxing treatments and use of surfactants, for example use of shampoo.

Preferred environmental assaults include, for example, humidity, pollution, hard water, salt water, ultra violet light, wind and temperature extremes.

Beneficial Treatments and Regimes

Preferred treatments and regimes are those that reduce or alleviate the effects of an assault to the hair. Effective treatments and regimes will restore desirable movement characteristics to hair following assault.

Preferred treatments for hair (step vi) are rinse off and leave on products. Preferred hair treatment compositions are selected from a shampoo, a rinse-off hair conditioner, a hair mask, a leave-on conditioner composition, and a pre-treatment composition, more preferably selected from a rinse-off hair conditioner, a hair mask, a leave-on conditioner composition, and a pre-treatment composition, for example an oil treatment, and most preferably selected from a rinse-off hair conditioner, a hair mask and a leave-on conditioner composition.

Rinse off conditioners for use in the invention are conditioners that are typically left on wet hair for 1 to 2 minutes before being rinsed off.

Hair masks for use in the present invention are treatments that are typically left on the hair for 3 to 10 minutes, preferably from 3 to 5 minutes, more preferably 4 to 5 minutes, before being rinsed off.

Leave-on conditioners for use in the invention are typically applied to the hair and left on the hair for more than 10 minutes, and preferably are applied to the hair after washing and not rinsed out until the next wash.

Treatments compositions for use in the method of the current invention preferably comprise conditioning agents. Conditioning agents are preferably selected from cationic surfactants, used singly or in admixture.

Cationic surfactants useful in compositions for use in the method of the invention contain amino or quaternary ammonium hydrophilic moieties which are positively charged when dissolved in aqueous composition.

Examples of suitable cationic surfactants are those corresponding to the formula

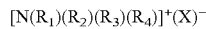

in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for compositions for use in the method of the present invention are monoalkyl quarternary ammonium compounds in which the akyl chain lengthy is $C_8$ to $C_{14}$.

Suitable examples of such materials correspond to the formula

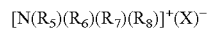

in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl cahins of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl cahins (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quarternary ammonium compounds of the above general formula for use in compositions for use in the method of the invention include:

(i) Lauryl trimethylammonium chloride (available commercially as Arquad C35 ex Akzo); cocodimethyl benzyl ammonium chloride (available commercially as Arquad DMCB-80 ex-Akzo)

(ii) Compounds of the formula:

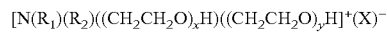

wherein:

x+y is an integer from 2 to 20;

$R_1$ is a hydrocarbyl chain having 8 to 14, preferably 12 to 14, most preferably 12 carbon atoms and containing ether, ester, amido or amino moieties present as substituent's or as linkages in the radical chain;

$R_2$ is a $C_1$-$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).

(iii) Compounds of the formula:

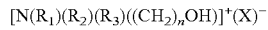

wherein:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$-$C_3$ alkyl groups, and are preferably methyl, and X− is a salt-forming anion such as those selected from halogen, (e.g. chloride, bromide), acetate, citrate, lactate, glycolate, phosphate nitrate, sulphate, alkylsulphate radicals. Suitable examples are lauryldimethylhydroxyethylammonium chloride (available commercially as Prapagen HY ex-Clariant).

Mixtures of any of the foregoing cationic surfactants compounds may also be suitable.

Examples of suitable cationic surfactants for use in hair compositions for use in the method of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 w.t. % of the total composition.

A preferred conditioner comprises a conditioning gel phase. Such conditioners and methods for making them are described in WO2014/016354, WO2014/016353, WO2012/016352 and WO2014/016351.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present invention may preferably comprise a miscellar structured liquid.

The pH of a conditioner comprising the present composition is preferably 3-5. More preferably the pH of the composition is 4.5-5.5.

Where the composition has a pH of less than 3.10 it is preferred that it is in the form of a conditioning mask for intense treatment.

Further conditioning ingredients include conditioning oils, preferably selected from coconut oil and olive oil.

Further preferred beneficial hair treatment compositions are styling compositions, which typically take the form of sprays, mousses, gels, waxes, serums or lotions. Such compositions can be used to modify the movement properties of hair.

Mousses, gels, waxes, serums and lotions are typically applied to hair by first dispensing onto the hand and then transferring onto the hair from the hand. Such application enables targeting deposition of the product to the parts of the hair where the user desires to change the movement characteristics. Foamed products such as styling mousses are a popular product format.

Styling compositions preferably comprise a hair styling polymer.

Hair styling polymers are polymers or resins that provide elements of style to hair, such as hold, general shape definition, shape retention, defined straightening, curling and so on, typically included in gels, mousses, serums, and hair sprays.

Some styling polymers are classed as film-forming polymers, which are often the source of "hold" in styling products such as hair gels and hairsprays. These polymers deposit onto the surface of the hair and then dry to form clear films that are strong and hold the hairs together until the film is either removed via washing or the film is broken due to mechanical forces on the hair (combing).

Examples include PVP (poly N-vinyl-2-pyrrolidone), PVA (polyvinyl acetate) and PVP/VA copolymer, amongst others.

Other styling polymers used in soft styling products, such as mousses are acrylate based, such as polyacrylates (for example polyacrylate-32, polyacylate-14), acrylates crosspolymers (for example acrylates crosspolymer-3, polyacrylate-2 crosspolymer) and AMO-acrylates/allyl methacrylate copolymer, amongst others.

Further examples of styling polymers include polyquaternium compounds, polyvinyl caprolactam copolymers and esters of PVM/MA(methyl vinyl ether and maleic anhydride).

Other preferred beneficial treatments are treatments such as anti-frizz or smoothing treatments. Compositions comprising oils for smoothing and reducing flyaway are also preferred.

Optional features of the invention will now be set out. These are applicable singly or in any combination with any aspect of the invention.

The method of the invention may be carried out using a single bundle of fibres. In a preferred method, two or more hair switches are mountable to the movement rig, wherein the same forced oscillation is applied simultaneously to the two or more hair switches.

In this way, both quantitative measurements of each individual hair switch, as well as comparative measurements (both quantitative and qualitative) between the two or more switches are possible. Each of the two or more switches may be treated with different hair products before the measurements take place. Accordingly, the apparatus enables quantitative comparisons of the effects on the bounce and movement of the hair switches arising as a result of the hair products used. Hair products applied to the hair switches may include one or more of: shampoo, conditioner, hair treatments, and hair styling products, for example.

The quantitative measurements for single or multiple switches may include one or more of: x amplitude; y amplitude; relative phase between the top and bottom of the hair switch; decay time; natural frequency; 2D area of the hair switch; change of 2D area of hair switch between before movement and after movement. Quantitative measurements of the 2D area of the hair switch, and how it changes during the steady state of movement, are also made. For example, minimum, maximum and average volume of the hair switch during steady state movement may be measured.

The measurement of X amplitude is a measurement of how far the hair switch moves in the horizontal, X axis.

The measurement of Y amplitude is a measurement of how far the hair switch moves in the vertical, Y axis.

The relative phase is a measurement of the difference in movement between the top and bottom of a given hair switch.

The decay time is the time taken for the hair switch to come to rest after the forced oscillation has been stopped.

The natural frequency is a measurement of the speed at which the hair switch moves (in the x and/or the y direction) after excitation by the forced oscillation is stopped.

The 2D area of the hair switch as viewed by the camera (i.e. the total volume in the image plane).

The change in 2D area of the hair switch before and after movement may also be referred to as the change in volume of the hair switch. In other words, the difference in volume of the hair switch as viewed by the camera, before and after movement, may be measured.

Generally, the switch may move as a main body of hair. However, stray hairs or small bundles of hairs may become detached from the main body of the hair. The existence of such stray hairs or small bundles of hairs (otherwise known as "flyaways") away from the main body of the hair switch may be identified. The present invention may be configured to apply a filter to exclude such detached stray hairs or small bundles of hairs from further analysis by ignoring them, thus excluding flyways in further analysis of the associated hair switch. In other words, a filter may be applied to the captured images to exclude any stray hairs detected before subsequent analysis of the images is carried out. The filter operates on the images to locate the outline of the hair switch, where the outline at least partially excludes stray fibres ("flyaways") that are located away from the main body of the hair switch. Ignoring flyaways in this way may improve hair spine location.

The filter may take the form of a minimum length ratio. The minimum length ratio may be a minimum value of the ratio of the length of a radius to the length of the switch. By excluding hairs that exceed such a minimum length ratio it is possible to exclude hairs that are widely separated from the main body of the switch (i.e. flyaways). Any hairs detected in the image which lie outside of this minimum length ratio may be considered to be spurious and ignored during subsequent analysis, which may include the determination of any one or more of the quantitative measurements mentioned above.

A second option for the filter may be an intensity threshold in the image. Stray fibres may typically have a lower intensity in the image, and consequently by applying an intensity threshold below which portions of the image are ignored, it is possible to implement a stray fibre filter.

A filter may comprise an intensity threshold component and a minimum length ratio component.

In some embodiments, the computer comprises an input for receiving consumer modelled data based upon consumer studies carried out using the hair switch(es).

This consumer modelled data received may typically take the form of a consumer perception value, "d prime" (d'), calculated by applying a Thurstonian model, or other latent variable model, to the consumer perception of relative differences between two or more hair switches for a particular hair attribute. The Thurstonian model is a latent variable model which maps the consumer impressions (from consumer studies) e.g. the consumer's impressions as to which sample of hair has the best "bounce", onto discrete ordered categories of response. Thurstonian models are known to provide a mechanism for sensory discrimination tasks.

The raw data obtained from consumer groups may relate to one or more different attributes of the hair, preferably bounce, lightweight movement, fluid movement and controlled movement.

These attributes are terms that are commonly used with respect to the movement of hair, and common terms used by consumers in the description of hair movement characteristics. In performing consumer studies no formal definitions of these attributes were provided to the consumers. It will be appreciated that differences in individuals' understanding and assessment of a given attribute are reduced by considering a larger population of consumers.

As described below, a predicted attribute value is generated for a given attributed is based on a model that has been created on the basis of consumer data related to that same attribute. For example, a predicted performance for the "bounce" attribute will be based on a "bounce" model that had, during its creation, consumer modelled data related to "bounce". In some embodiments, upon receiving quantitative measurements of a hair switch, the processor applies a cross-validated model which combines the quantitative measurements of the hair switches used in model generation with the consumer modelled data (which comes from consumer studies of the same hair switches that have been used for the cross-validated model generation).

The cross validated model provides a correlation between the quantitative measurements of a set of hair switches and consumer perception values for the same set of switches. It will be appreciated that a number of modelling methods may be suitable for modelling such correlations. One example of a cross validated model is a partial least squares (PLS) model, which correlates quantitative measurements derived from the captured images with the consumer perception values (d') extracted from the consumer modelled data.

A particular cross-validated model may include a number of attribute models. Each attribute model may itself be a cross-validated model in respect of a single particular movement attribute. For example, a particular cross-validated model may include an attribute model for each of bounce, lightweight movement, fluid movement, and controlled movement.

In some embodiments, the processor is further configured to apply a predictive model to new hair switches (i.e. hair switches not used in generating the cross-validated model). The predictive model may be based upon the cross-validated model. The predictive model can be used to analyse lab measurements of new data (i.e. quantitative measurements of new hair switches) and predict consumer responses based upon the predictive model, which in turn is based upon the cross-validated model(s).

In this way, the apparatus uses lab-based data in the form of cross-validated models to predict a consumer response, thereby enabling the benefits of a consumer study to be achieved without the need to set up and conduct expensive and time consuming consumer studies. In other words, the earlier consumer studies used to produce the cross-validated models act as a calibration tool, such that consumer responses can be predicted for later measurements of hair switches taken on a movement rig.

Further optional features of the invention are set out below.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

Figure 1:
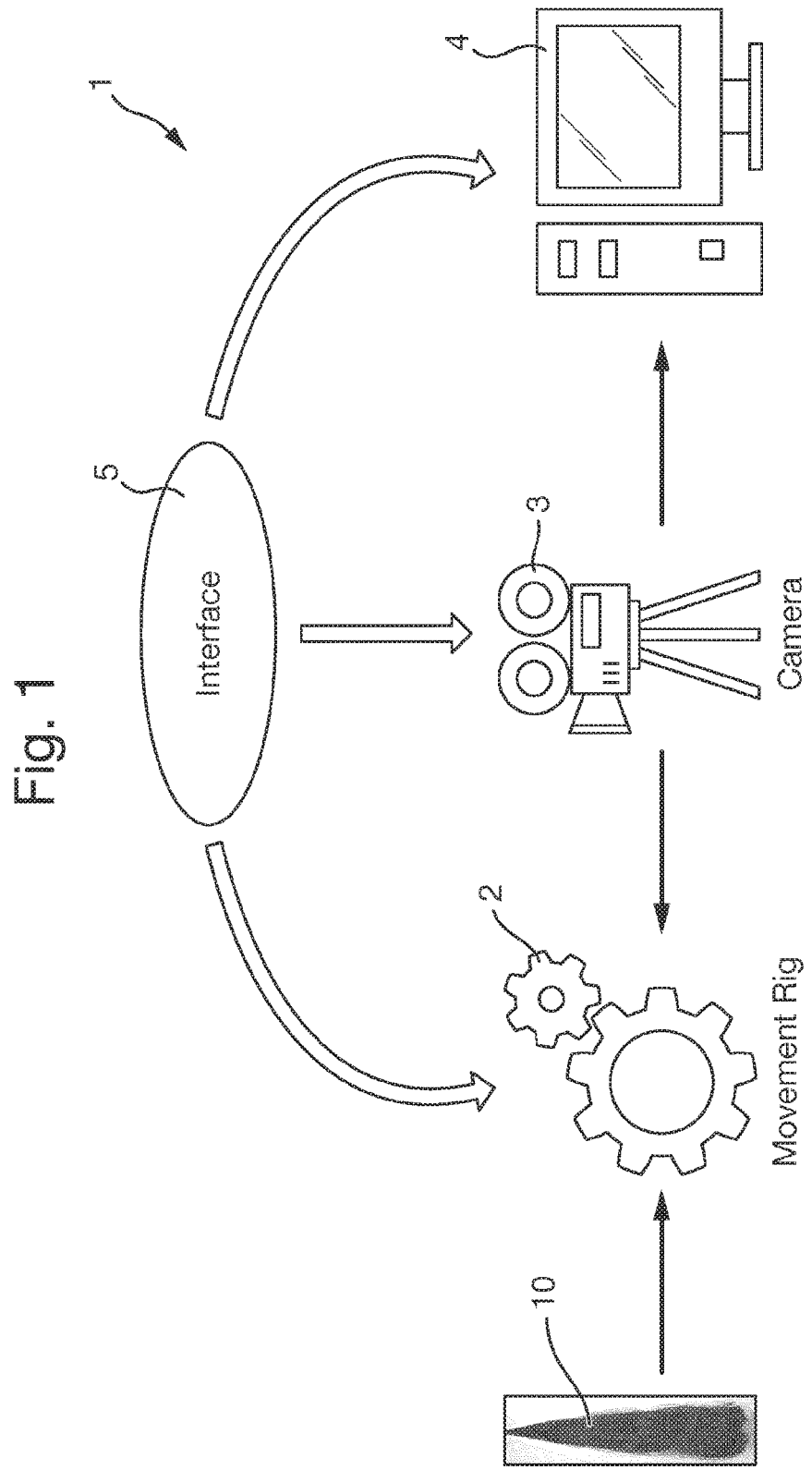
FIG. 1 shows a schematic diagram of an apparatus for use in the method of the present invention.

The apparatus used in the method the present invention is preferably configured to measure characteristics of movement of one or more hair switches as described below in more detail with reference for FIGS. 1, 2 and 3. These characteristics (also known as "movement parameters") may include quantitative measurements of: x amplitude; y amplitude; relative phase between the top and bottom of the hair switch; decay time; frequency; 2D area of the hair switch, and; change on 2D area before and after movement.

The apparatus for use in the method of the present invention may also be configured to apply a filter to exclude stray fibres located away from the body of the hair switch from further analysis by ignoring them. The measured movement characteristics can, in turn, be used to deduce attributes of hair movement such as: bounce and fluid movement for the one or more hair switches 10, 10a, 10b. A number of other attributes of hair movement may be also be defined. For example, flexibility during movement; keeping shape/style/alignment during movement; less "weighed down" during movement; lightweight movement, and lively movement.

Such attributes may be applicable in a number of different countries (for example, UK, US, China, Japan, Indonesia, India, Thailand and Brazil). Of course, attributes could equally be useful in all countries Some other attributes may be particularly applicable for consumers in particular countries. For example, weighty (in Thailand); Sa-Luay (in Thailand); flows beautifully/naturally (in Thailand); moves with vitality (in Indonesia), and; sarasara sensory (in Japan).

The apparatus 1 includes a movement rig 2 upon which the hair switch is mountable. Typically, this includes a bar (not visible in FIG. 2) which includes multiple switch holders, each switch holder for engaging the top of a respective hair switch. The movement rig includes a motor which applies an oscillatory force (the forced oscillation) in the horizontal axis to the bar, causing it to undergo an oscillating movement in the direction denoted "x".

It will be appreciated that the oscillation frequency can take a range of suitable values. For example, a suitable range may be 0.8 to 1.3 Hz. There may be lower frequency, below which oscillatory movement of the switch is not induced, rather the whole switch moves rigidly with the forced oscillation. There may an upper frequency, above which undesirable movements of the hair switch are induced (for example, twisting movements). A preferred oscillation frequency of the bar may be 1.0 Hz. Equally, the oscillation frequency could be a different, suitable, value. It will be appreciated that a number of factors are important in determining the forced oscillation frequency, there may be no strict limits to the forced oscillation frequency. By attaching all hair switches to the single bar, any movement of the bar will cause the same force of movement to be applied to each mounted hair switch 10a, 10b.

The forced oscillation frequency used when making the quantitative measurements of the hair switches used in the generation of the cross validated model may be identical to the forced oscillation frequency used for the quantitative measurements of hair switches used as an input to the corresponding predictive model.

Figure 2:
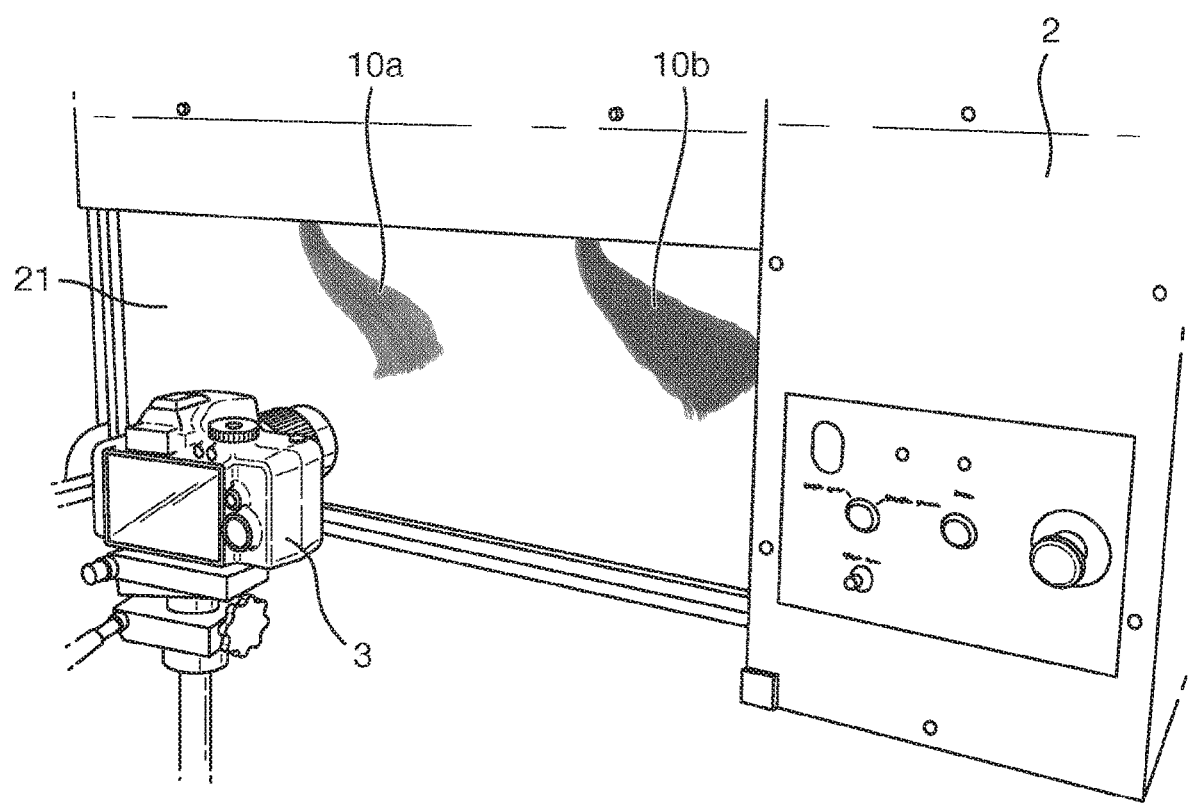
FIG. 2 depicts the movement rig and camera of the apparatus in more detail.

In the embodiment shown in FIG. 2, the bar is located in front of a lightbox 21. A camera 3, specifically a camera with video capabilities, is mounted at a fixed distance from the lightbox 21 for capturing images of the hair samples (via frames of a video), not only during the initial excitation and the time at which the bar is oscillating (and where the mounted hair switches therefore undergo steady state movement); but also for a period of time after the bar has finished oscillating, where the mounted hair switches undergo motion decay. In this way, the camera is able to capture images of the hair movement during forced oscillation; but also, images of the decay of movement after the forced oscillation has ceased to be applied.

The images may be obtained from a video that is recorded using the camera. The images are extracted from the video. Each image may correspond to a frame of the video. Re-analysis of the images from a particular video may also be possible without having to re-extract the images from the video. In other words, the images may be extracted from the video only once, and then stored. The stored images are then available for analysis without having to repeat the step of extracting the images from the video.

A delay may be applied between the start of recording by the camera 3, and the start of forced oscillation movement by the movement rig 2. As an example, this delay may have a magnitude of 1 second or more; the motion run time during which the bar is oscillated may have a duration of 7 seconds or more; and the delay between the stop of forced oscillation (by stopping the movement of the bar) and the time at which the camera stops capturing images, may have a value of 6 seconds or more. It will be appreciated that these time periods are examples only.

The apparatus 1 further comprises a computer 4 which is communicably connected to the camera 3, the computer including a processor for processing the images and/or videos captured by the camera 3, and for extracting quantitative measurements of the hair switch from the captured images.

The computer 4, camera 3 and movement rig 2 may be interfaced via an interface 5 such as a wireless network. In this way, programs running on the computer may also be used to control the movement rig and camera, in particular start and stop times.

The measurement and analysis software run by the processor to process the images and extract measurements may be written on any suitable platform, such as Exelis IDL version 8.3 or later versions, an important feature being the inclusion of a function such as the IDL function IDLffVideoRead, which performs conversion of the video files obtained into images. The presence of purpose built software for image analysis functions such as the IMF_ImageAnalysis library in Exelis IDL version 8.4 may also be advantageous.

Suitable cameras include, but are not limited to the Nikon D90, Nikon D5000 and Nikon D3200 cameras. Cameras such as the D3200 were found to be particularly advantageous as they enable the user to set the shutter speed in manual video mode. Shutter speeds of 1/500 s and 1/1000 s were tested and both worked well, with 1/1000 s performing particularly well. Cameras such as the D90 and D5000, which do not allow for variable shutter speed when taking videos may result in motion blur, which makes the switch outline more indistinct and subsequent measurements obtained less accurate. It will be appreciated that these cameras are examples only, and many other cameras may be capable of the technical performance detailed herein.

The maximum video frame rate for the D3200 was 25 frames per second progressive scan (25p) with image size of 1920 by 1080. Higher frame rates that are only available at lower spatial resolution Interlaced video modes, such as 50i, should be avoided, because they are composed of two separate exposures interlaced together and the motion between exposures may create a double image.

As well as measurement and analysis of a single hair switch, measurements and analysis can be carried out by the software on multiple switches 10a, 10b, which are simultaneously mounted on the movement rig. In the case of multiple switches, the number of switches may form an input to the software, and the software will try to find in the images the number of switches input to the software. The apparatus may be configured to give an error if the specified number of switches cannot be identified within the field of view of the camera.

The apparatus also includes a calibration disc (not shown) located within the field of view of the camera. The calibration disc has a known size, thereby providing a mechanism for calibrating the pixels of the captured images into real space measurements.

Figure 3:
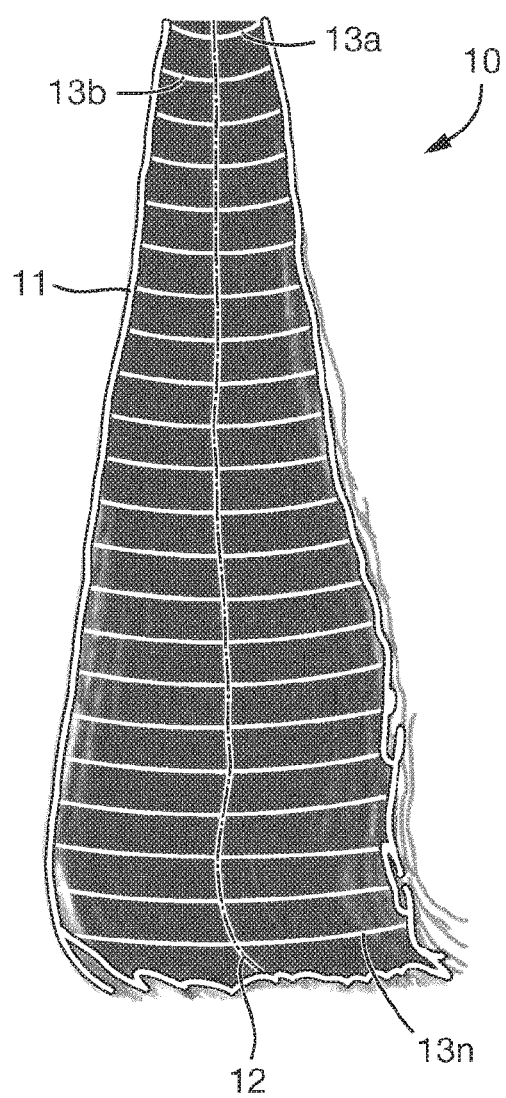
FIG. 3 depicts a captured screenshot image of a hair switch in motion, the captured image being analysed to obtain quantitative measurements of the hair switch.

An example of a captured image of a hair switch is shown in FIG. 3, the captured image being analysed to obtain quantitative measurements of the hair switch. Initially, for each hair switch in the image, the software extracts the switch outline 11 and the spine 12 of the hair switch. The software then analyses the movement parameters at multiple equally spaced radii 13a, 13b . . . 13n along the length of the switch. In the example shown, the spacing between adjacent radii is 10 mm.

Equations used to analyse the motion of a particular hair switch are set out below for each of the steady state (forced oscillation) (equation (1) and the decay time (equation (2)) (after forced oscillation).

Steady state:

$$x = A\sin\left(\frac{2\pi t}{\lambda} + \frac{\pi \varphi}{180}\right) + B \quad (1)$$

Decay state $$x = A\sin\left(\frac{2\pi t}{\lambda} + \frac{\pi \varphi}{180}\right)e^{\frac{-(t-T_2)}{\tau}} + B \quad (2)$$

where:

x is the horizontal location of the crossing point of the spine and a particular radius in mm;

A is the amplitude in mm;

t is the time in seconds;

T2 is the time in seconds when the forced motion is stopped;

$\lambda$ is the wavelength in seconds;

$\varphi$ is the phase angle in degrees;

$\tau$ is the motion decay time constant in seconds;

B is the offset in mm.

The modelled mathematical form of motion in the x-direction is sinusoidal (as above). The root-mean-squared (RMS) value of the sinusoidal motion described above is RMS=A/sqrt(2). The RMS is equal to the standard deviation of the x-values, which means that the amplitude, A=sqrt(2)*standard deviation(x_position values).

For motion in the y-direction, the Amplitude of the y-direction motion is calculated as A_y=sqrt(2)*standard deviation(y_position values).

Measurement and analysis steps carried out by software run on the processor of the computer are described in more detail below with reference to FIGS. 4 to 9.

Figure 4:
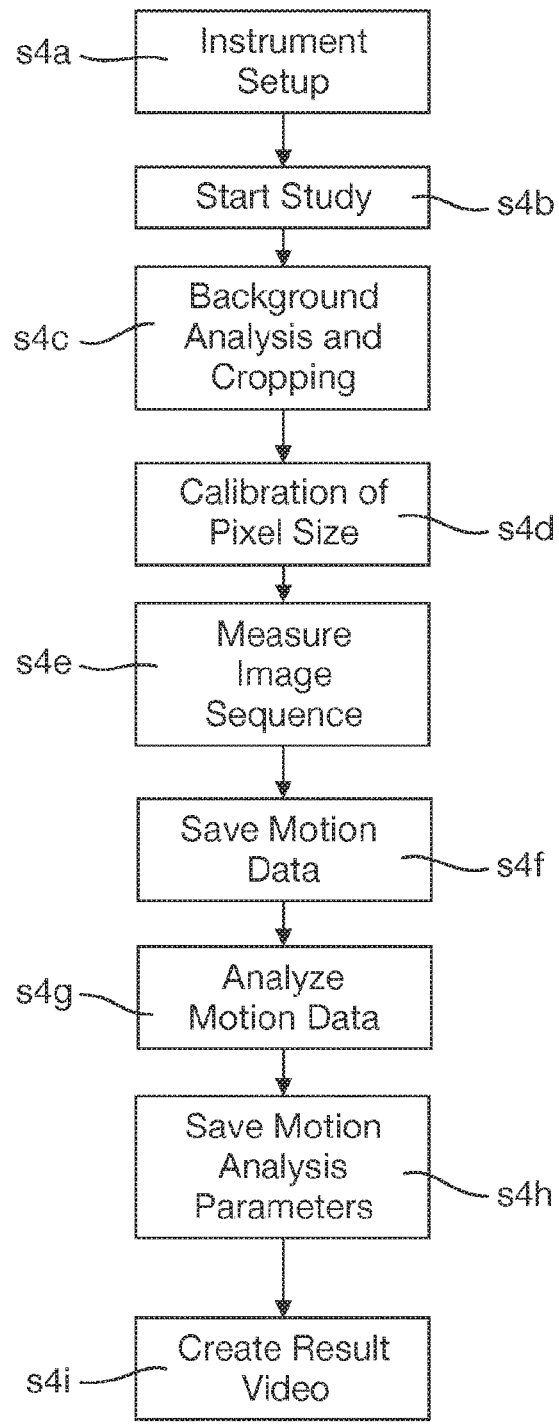
FIG. 4 shows an overview of the method of obtaining quantitative measurements using the measurement rig.

FIG. 4 shows an overview of an example of a method of obtaining quantitative measurements using the measurement rig.

In an initial instrument setup step s4a the apparatus is provided as described above in relation to FIGS. 1 and 2. In finer detail, one or more of the following sub-steps are carried out.

Parameters to be used during measurement are loaded or defined by the software. Such parameters may include: Motion speed, Motion amplitude, Motion Start time, Motion End time, Motion Decay time, video frame rate, video width and height, video shutter speed and lens aperture, number of switches, number of cycles of forced oscillation to ignore before start of Steady State region, Switch measurement radial separation (mm), maximum radius (mm) and/or Calibration disc size (mm);

Instrumental set up includes setting the focus the camera such that it is focused on each of the one or more hair switches to be analysed.

A short video of the background is captured and converted to a single image, typically labelled as "Background" and a short video of the calibration disc is captured and converted to a single image, typically labelled "Calibration".

In a subsequent step s4b, the study is started. This includes entering switch details, such as the number of switches. The type of each hair switch and treatments applied to each of the hair switches may also be noted. The video capture of hair switch or switches is started at start time T0; T0 is noted.

The forced oscillation motion of the bar is started, the time of starting the oscillation motion relative to T0, TS, is noted.

The forced oscillation motion of the bar is stopped, and the stop time TE, relative to T0, is noted.

After a given period of time from TE, which is chosen to capture the decay of motion of the hair switch(es), the video recording is stopped.

In subsequent steps s4c and s4d, background analysis, cropping, and calibration of the captured images are carried out. This includes: converting the video file of the background to a single background image, converting the video file of calibration disc to a single calibration disc image, and extracting from the video file of switch motion a sequence of images for analysis.

The lightbox region in the background image is identified by identifying crop coordinates, which correspond to the lightbox region s4c.

To calibrate the pixel size from the calibration disc image s4d, the calibration disc is identified in the calibration disc image. The known size of the calibration disc is used to calculate pixel size in the real-world.

In a subsequent step, the image sequence of the desired switch(es) forced movement and decay is measured. The cropped/calibrated images may be stored.

In a subsequent step, s4f, the motion data obtained is stored.

Motion data is then analysed s4g, including the following analysis steps:
Determining the start of motion time, T1 using top of switch motion data together with TS and TE;
Determining the end of motion time, T2, using top of switch motion data together with TS and TE;
Fitting a sine wave to top of switch data, returning $A_0$, $\lambda_0$, $\varphi_0$ and $B_0$;
Determining the start of steady state region, using motion start time, fit and Nc, where Nc is the number of cycles of oscillation at the start of the forced oscillation that are to be ignored before starting the steady state region.
Determining the end of steady state region and the start of the decay region, corresponding to T2;
Fitting sine waves to each radius switch data between T1 and T2, and returning $A_i$, $\lambda_i$, $\varphi_i$ and $B_i$; each point that is fitted corresponds to an intersection of the spine and a respective radius;
Fitting decaying sine waves to each radius switch data between T2 and TE, and returning motion analysis parameters $A_i$, $\lambda_i$, $\varphi_i$, $\tau_i$ and $B_i$; each point that is fitted corresponds to an intersection of the spine and a respective radius;

In a subsequent step, the motion analysis parameters are saved s4h.

If desired, a result video is created using the result image files.

The software may provide a user with different options to:
Capture switch motion and measure the motion for an isolated video or;
Capture several switch videos and then analyse the videos afterwards.

What is claimed is:

1. A method of measuring changes in hair movement characteristics, predictive of consumer response, the method comprising the steps of:
   i) providing an apparatus, including a camera for capturing images of hair, for measuring hair movement characteristics of hair;
   ii) measuring the hair movement characteristics using the apparatus to obtain a first hair movement characteristic;
   iii) applying a treatment to the hair or an assault to the hair;
   iv) measuring the hair movement characteristics using the apparatus after step iii) to obtain a second hair movement characteristic;
   v) comparing the first hair movement characteristic and the second hair movement characteristic; and
   vi) assessing a change in movement occurring as a result of the application of the treatment or the assault.

2. The method of claim 1, wherein steps (iii) to (vi) are repeated from 2 times to 20 times, inclusive.

3. The method of claim 1, wherein:
the first hair movement characteristic comprises at least one of: bounce, fluid movement, flexibility during movement, keeping shape/style/alignment during movement, less "weighed down" during movement, or lively movement; and the second hair movement characteristic comprises at least one of: bounce, fluid movement, flexibility during movement, keeping shape/style/alignment during movement, less "weighed down" during movement, or lively movement.

4. The method of claim 1, wherein: comparing the first hair movement characteristic and the second hair movement characteristic results in a difference; and
assessing the change in movement comprises comparing the difference to a scale.

5. The method of claim 4, wherein the scale comprises indicators that correspond to incremental levels of hair movement characteristics.

6. The method of claim 1, wherein the apparatus comprises:
a rig upon which the hair is mountable, the rig operable to apply a farced oscillation to the hair;
a camera for capturing mages of the hair during movement of the hair during and after application of the forced oscillation;
a computer communicably connected to the camera, the computer including —a processor; capable of processing the images and extracting quantitative measurements of the hair rom the images.

7. The method of claim 6, further comprising the step of applying a filter to the images to remove any stray hairs detected before subsequent analysis of the images is carried out.

8. The method of claim 6, further comprising the step of receiving at an input of the computer, consumer modelled data based upon consumer studies carried out using the hair switch(es).

9. The method of claim 8, wherein, upon receiving the consumer modelled data, the processor applies a cross-validated model which combines the quantitative measurements with the consumer modelled data.

10. The method of claim 9, wherein the cross-validated model is a partial least squares model which correlates the quantitative measurements with consumer perception values extracted from the consumer modelled data.

11. The method of claim 10, further comprising the step of applying a predictive model based upon the cross-validated model to quantitative measurements taken from new sets of hair switches, the predictive model predicting consumer responses to the new sets of hair switches based upon the cross-validated model.

12. A method of obtaining a hair movement characteristic of a hair switch using an apparatus having a camera that is configured to obtain images of the hair switch, a rig that is configured to support the hair switch and be selectively oscillated while the hair switch is supported on the rig, and a computer that is configured to analyze the images, the method comprising:
  causing the camera to obtain a first image of the hair switch; causing the rig to be oscillated after obtaining the first image;
  causing the camera to obtain a second image of the hair switch while causing the rig to be oscillated;
  causing the computer to analyze the first image to obtain a first quantitative measurement;
  causing the computer to analyze the second image to obtain a second quantitative measurement;
  comparing the first quantitative measurement and the second quantitative measurement to obtain a first difference; and
  determining a hair attribute based on the first difference.

13. The method of claim 12, wherein causing the rig to be oscillated after obtaining the first image comprises causing the rig to be oscillated at a frequency of 1 Hertz.

14. The method of claim 12, further comprising causing the camera to obtain a third image of the hair switch after causing the rig to be oscillated.

15. The method of claim 14, further comprising;
  causing the computer to analyze the third image to obtain a third quantitative measurement; and
  comparing the third quantitative measurement to at least one of the first quantitative measurement or the second quantitative measurement, to obtain a second difference;
  wherein the hair attribute is determined based on the first difference nd the second difference.

16. A method of obtaining a hair movement characteristic of a hair switch using an apparatus having a camera that is configured to obtain images of the hair switch, a rig that is configured to support the hair switch and be selectively oscillated while the hair switch is supported on the rig, and a computer that is configured to analyze the images, the method comprising:
  causing the rig to be oscillated;
  causing the camera to obtain a first image of the hair switch while causing the rig to be oscillated;
  causing the camera to obtain a second image of the hair switch after causing the rig to be oscillated;
  causing the computer to analyze the first image to obtain a first quantitative measurement;
  causing the computer to analyze the second image to obtain a second quantitative measurement;
  comparing the first quantitative measurement and the second quantitative measurement to obtain a first difference; and
  determining a hair attribute based on the first difference.

17. The method of claim 16, wherein causing the rig to be oscillated comprises causing the rig to be oscillated at a frequency of 1 Hertz.

* * * * *